United States Patent [19]
Miyamoto et al.

[11] Patent Number: 6,153,242
[45] Date of Patent: Nov. 28, 2000

[54] METHOD FOR PREPARING SNACK FOOD

[75] Inventors: Hiroyuki Miyamoto; Kazuyo Kobayashi, both of Higashi-Osaka, Japan

[73] Assignee: House Foods Corporation, Higashi-Osaka, Japan

[21] Appl. No.: 09/228,192

[22] Filed: Jan. 11, 1999

[51] Int. Cl.[7] .............................. A21B 1/26; A23L 1/217
[52] U.S. Cl. .................. 426/446; 426/448; 426/523; 426/808
[58] Field of Search ................................ 426/445, 446, 426/448, 512, 518, 808, 559, 94, 523

[56] References Cited

U.S. PATENT DOCUMENTS

| | | | |
|---|---|---|---|
| 3,502,479 | 3/1970 | Singer et al. | 99/100 |
| 4,525,367 | 6/1985 | Allison | 426/394 |
| 4,965,081 | 10/1990 | Lazarus | 426/242 |
| 5,188,859 | 2/1993 | Lodge et al. | 426/560 |
| 5,614,239 | 3/1997 | Tedesco | 426/445 |

FOREIGN PATENT DOCUMENTS

| | | |
|---|---|---|
| 0 331 820 | 9/1989 | European Pat. Off. . |

*Primary Examiner*—Nina Bhat
*Attorney, Agent, or Firm*—Oblon, Spivak, McClelland, Maier & Neustadt, P.C.

[57] ABSTRACT

A method for preparing a snack food comprises the steps of subjecting dough for snack foods to a puffing treatment through hot-air drying and then incorporating, into the puffed snack dough, oils and fats having a saturated fatty acid content of not more than 40% and an unsaturated fatty acid content of not less than 50%, as an oil and fat component. The method permits the preparation of a snack food that makes it possible to provide the smooth and easy melting ability of the oil and fat component in the mouth, which has light taste and texture and leaves a pleasant aftertaste.

23 Claims, No Drawings

METHOD FOR PREPARING SNACK FOOD

FIELD OF THE INVENTION

The present invention relates to a method for preparing a snack food and more specifically to a method for preparing a snack food, which makes it possible to provide the smooth and easy melting ability of oils and fats in the mouth, and to leave a pleasing aftertaste in the mouth, and which is suitable as a recent health-directing food.

DESCRIPTION OF THE BACKGROUND

There has long been known a method for preparing a snack food by subjecting dough for snack foods to puffing through an oil-frying treatment. According to this method for oil-frying a snack dough, the resulting snack food would have a smooth and easy melting ability in the mouth because of the presence of oils and fats used for the oil-frying treatment. However, such a conventional snack food suffers from various problems. For instance, it leaves a bad aftertaste in the mouth because it has a heavy or greasy taste of the oils and fats used for oil-frying; and the snack food would absorb a large quantity of oils an fats during the oil-frying step. Moreover, it has a high content of an oil and fat component, and accordingly, such a conventional snack food would not be appropriate for the recent health-oriented purpose.

To solve the foregoing problems associated with the conventional oil-frying method, there has been proposed a method comprising the steps of puffing dough for snack foods by hot-air drying and then incorporating a small amount of oils and fats into the hot air-dried snack dough. However, the snack food thus prepared has still left a bad aftertaste in the mouth and has thus still been insufficient in the flavor and taste.

SUMMARY OF THE INVENTION

Accordingly, an object of the present invention is to provide a method for preparing a snack food which has a smooth and easy melting ability in the mouth, can leave a pleasing aftertaste and has good flavor and thus can be admitted by the recent health-oriented people.

The inventors of this invention have conducted vigorous studies to eliminate the foregoing drawbacks associated with the snack food prepared according to the conventional oil-frying method in order to develop a novel technique for producing a snack food which makes it possible to provide the smooth and easy melting ability of oils and fats in the mouth, and to leave a pleasant aftertaste, which is excellent in flavor and which is well-adapted for the recent health-directing tendency. As a result, the inventors have found that the desired effects of the present invention can be accomplished by subjecting snack dough to a puffing treatment through hot-air drying and thereafter incorporating, into the hot air-dried dough, an oil and fat component which has a specific saturated fatty acid content and a specific unsaturated fatty acid content, and thus have completed the present invention on the basis of the foregoing finding.

According to the present invention, the foregoing object of the present invention can effectively be accomplished by providing a novel method for preparing a snack food, which comprises the steps of subjecting dough for snack foods to a puffing treatment through hot-air drying and then incorporating, into the hot air-dried snack dough, an oil and fat component which has a saturated fatty acid content of not more than 40% and an unsaturated fatty acid content of not less than 50%, based on the total weight of the oils and fats used.

DESCRIPTION OF THE PREFERRED EMBODIMENTS

The method for preparing a snack food according to the present invention will be further described in more detail below.

In the method for preparing a snack food according to the present invention, dough for snack foods is first prepared by the usual method. As raw materials used for the preparation of snack dough employed in the method of the present invention, any starch materials that can be used for the preparation of snack foods may be used without any restriction. Specific examples thereof include maize (corn), potato, wheat, rice, or these raw materials which are processed, for instance, powdery raw materials such as potato starch, corn starch, wheat starch and rice starch. In this respect, these raw starch materials may be used alone or in any combination of at least two of them in the present invention. Thus, the foregoing raw starch material may be pregelatinized and then the pregelatinized starch material is formed into a desired shape followed by cutting the material to give desired snack dough.

The method for pregelatinization of the foregoing raw starch material is not restricted to any specific one and the material may be pregelatinized by any conventionally known method. More specifically, there may be used, for instance, a method which comprises the steps of adding water to the foregoing raw material, mixing them, and then pregelatinizing the mixture in a steaming-kneading machine; and a method which comprises the step of introducing the raw material and water into an extruder to thus simultaneously mix and pregelatinize them. In this connection, it is preferred in the present invention that the raw material is mixed with water and then the resulting mixture is pregelatinized.

Among the foregoing methods, preferred is a method in which the pregelatinization of the starch raw material is carried out in an extruder. This is because this method permits the uniform kneading of the material within a short period of time, the preparation of fine-grained dough and the resulting snack food shows a more excellent melting ability in the mouth. If the pregelatinization of the raw material is performed by an extruder as described above, the temperature and the time of the pregelatinization step preferably range from 100 to 180° C. and 5 to 40 seconds, respectively.

In the foregoing pregelatinization treatment, it is also possible to appropriately add, to the foregoing starch raw material, other proper additives such as sugar, common salt, chemical seasonings, pulverized products of, for instance, vegetables or other ingredients commonly used in this field.

The method for forming and cutting the foregoing pregelatinized starch raw material into pieces having a desired shape and size to thus give snack dough is not likewise limited to any particular one and there may be listed, for instance, a method in which the foregoing pregelatinized raw material is formed into a sheet by passing the material through the gaps formed between a plurality of rolls and then the sheet is cut into pieces having a desired shape and a size; and a method comprising extruding the pregelatinized raw material through a die placed at the tip of the extruder in an appropriate shape such as a coil or a ribbon and then cutting it into pieces having a predetermined length. In addition, it is desirable in the present invention that the snack dough be pre-dried prior to the hot-air drying as will be detailed below to thus control the moisture content of the dough to the range of from 4 to 10% by weight and preferably 5 to 9% by weight based on the total weight of the snack dough. This is because if the moisture content of the snack dough is controlled such that it falls within the range defined above, the snack dough can be regularly and uniformly puffed in the subsequent hot-air drying step. The means for the foregoing pre-drying procedure may be, for instance, a method comprising drying the sheet-like dough in a thermo-hygrostatic chamber so that the moisture present in the dough is not rapidly removed through evaporation. The pre-drying is preferably carried out at a temperature ranging from 20 to 60° C., a relative humidity ranging from 20 to 80% for a time of at least one hour. In this respect, if the pre-drying is carried out for at least 10 hours, the moisture content in the snack dough can be made uniform (tempering) throughout the dough.

In the method of the present invention, the snack dough thus obtained is then subjected to a puffing treatment through hot-air drying. The method for hot-air drying is not limited to any specific one, but preferred is, for instance, a fluidized-bed drying method. The fluidized-bed method comprises, for instance, supplying the sheet-like snack dough onto a flow-controller such as a porous plate, upwardly or downwardly blowing hot air on the sheet-like dough to thus dry the sheet-like dough while suspending and fluidizing the dough within the hot air; or supplying the sheet-like dough onto the conveying plane of a transporting conveyor which passes through a chamber provided with a hot air blower and blowing hot air on the sheet-like dough which is transported through the chamber to thus dry the dough, while suspending and fluidizing the dough within the chamber. The foregoing fluidized-bed drying method permits the uniform heat-transfer throughout the snack dough so that the dough is uniformly and regularly puffed. In this connection, the foregoing fluidized-bed drying can be carried out using, for instance, commercially available usual fluidized-bed roasting device or a conveyor dryer. The fluidized-bed drying procedure is preferably carried out for 10 to 40 seconds using hot air having a temperature ranging from 200 to 300° C.

It is important, in the method of the present invention, to subject the snack dough to a puffing treatment through hot-air drying and thereafter to incorporate oils and fats having a saturated fatty acid content of not more than 40% and preferably not more than 30% and an unsaturated fatty acid content of not less than 50% and preferably not less than 60% into the puffed snack dough, as has been discussed above. The incorporation of the foregoing oils and fats into the puffed snack dough in combination with the use of the following ingredients having a low oil and fat content and having a specific composition, as will be detailed below, would permit the production of a snack food which makes it possible to provide the smooth and easy melting ability of the oils and fats in the mouth, which is excellent in flavor and which can ensure high quality, in particular, in both the taste and texture and the health of the consumers. In this respect, most of the oils and fats commonly used in the snack foods prepared by the oil-frying method are those having a high saturated fatty acid content such as hardened oils in order to prevent, for instance, any effect of thermal oxidation during oil-frying and therefore, they are different from those used in the present invention.

Examples of the foregoing oils and fats include, but are not limited to, olive oil and rape seed oil. These oils and fats may provide oil and fat components each having specific contents of saturated and unsaturated fatty acids as defined above. Alternatively, it is also possible to use various combinations of a variety of vegetable oils and fats such as the foregoing oils and fats and soy bean oil and a variety of animal oils and fats such as lard, which are blended in such a manner that the saturated and unsaturated fatty acid contents each falls within the range defined above. Moreover, oils and fats may likewise be prepared artificially so that the saturated and unsaturated fatty acid contents each falls within the range defined above or such artificially prepared oils and fats may be used in combination with other oil and fat components. In this regard, oils and fats having a high content of monounsaturated fatty acids, among others, permit the production of a snack food having excellent quality from the viewpoint of, in particular, in the consumer's health. For this reason, preferably used in the present invention is olive oil.

The amount of the foregoing oils and fats in the snack food is not particularly restricted, but the content of oils and fats present in the snack food as a final product is desirably limited to not more than 10% by weight (hereinafter simply referred to as "%"), preferably 1 to 5% and more preferably 2 to 3% as expressed in terms of the crude fat content to thus make it possible to smoothly and easily melt the oils and fats in the mouth, to ensure the low oil and fat content of the resulting snack food from the viewpoint of the health of the consumers. In this connection, the foregoing oils and fats may appropriately be incorporated into the snack food by any known method such as spraying, coating and immersing methods.

Moreover, if the snack food is prepared by the method detailed above, the foregoing oils and fats can likewise be incorporated into the snack food after any flavoring material is adhered to the puffed snack dough using an adhesive liquid such as a starch solution. More specifically, an adhesive liquid to which flavoring materials are added is sprayed or coated on the puffed snack dough or an adhesive liquid free of any flavoring material is first applied onto the dough through spraying or coating and then flavoring materials are incorporated into the puffed sack dough; followed by drying the dough in, for instance, an oven. Subsequently, the oil and fat component is incorporated into the snack dough. Thus, the flavoring material can firmly be adhered to the snack food to thus give a variety of flavor to the snack food. Moreover, the oils and fats are added to the food after drying and accordingly, the oils and fats never undergo any thermal oxidation during production procedures.

In the method of the present invention, examples of raw materials for giving a variety of flavor to the snack food desirably include powdery ones such as common salt, meat, chicken, sea foods, cream, butter, onion, garlic, basil, spices. The amount of the foregoing flavoring material to be incorporated into the snack food desirably ranges from 2 to 12% and preferably 4 to 10% on the basis of the weight of the puffed snack dough. In addition, the foregoing adhesive liquid preferably used in the invention is a starch solution prepared by mixing, with water, about 1 to 2% (as expressed in terms of the solid content) of soluble starch, dextrin, corn syrup solid and/or corn syrup. The amount of the foregoing adhesive liquid to be used desirably ranges from 3 to 15%, preferably 5 to 10% based on the weight of the puffed snack dough.

The method of the present invention will be described below in more detail with reference to the following non-limitative working Examples. In the following description, the term "part" represents "part by weight" unless otherwise specified.

EXAMPLE 1

A mixture of 57 parts of corn flour, 14.3 parts of potato starch, 3.2 parts of granulated sugar, 0.8 part of common salt and 24.7 parts of water was supplied to a twin-screw extruder and to process them therein at a barrel temperature of 140° C. for 7 seconds to thus pregelatinize the corn flour and potato starch. Thereafter, the processed mixture was extruded through the die in the form of a coil, followed by cutting the coil into pieces having a length of 30 mm to give snack dough having a thickness of 0.8 mm. The moisture content of the resulting snack dough was found to be 30.0% by weight. Then the snack dough thus prepared was dried and tempered at a temperature of 40° C. and a relative humidity of 40% for 16 hours in a thermo-hygrostatic chamber, while blowing hot air on the snack dough at a velocity of 0.5 m/sec to thus control the moisture content of the dough to 5.85% by weight.

Then the snack dough thus produced and having a moisture content of 5.85% by weight was subjected to a fluidized-bed drying operation in a conveyor dryer while supplying hot air maintained at 260° C. for 26 seconds to thus puff the snack dough. The puffed snack dough was uniformly puffed while maintaining the coil-like shape thereof and having more attractive hollow cylindrical appearance. The dough was found to have a moisture content of 1.22% by weight.

Then a starch solution prepared by dissolving 20 parts of corn syrup powder (available from N-TACK, National Starch & Chemical Company) in 80 parts of water was sprayed on the puffed snack dough in a rate of 5 g of the starch solution per 100 g of the puffed dough, followed by addition and adhesion of 6 g of powdery sea food, 0.2 g of common salt and 0.4 g of butter powder, drying with heating in an oven at 100° C. for 5 minutes and finally spraying 3 g of olive oil on the puffed snack dough to form a snack food according to the present invention.

It was confirmed that the foregoing snack food contained about 3% of the oil and fat component, which comprises about 12% of the saturated fatty acid moiety and about 86% of the unsaturated fatty acid moiety (the rate of the monounsaturated fatty acid moiety: about 75%) as expressed in terms of the crude fat content.

When eating the snack food thus prepared, it was found that the snack food had a smooth and easy ability of melting in the mouth, excellent flavor and odor which make the most use of the flavor of flavoring materials such as powdery sea foods, did not have any greasy taste, had light flavor and taste, left a pleasant aftertaste in the mouth. Moreover, it had a low content of oils and fats and therefore, it would be adapted for the health-oriented consumers.

As has been described above in detail, the method for preparing a snack food according to the present invention comprises subjecting snack dough to a puffing treatment through hot-air drying and thereafter incorporating, into the puffed snack dough, an oil and fat component having a saturated fatty acid content of not more than 40% and an unsaturated fatty acid content of not less than 50%. Such construction of the present invention permits the preparation of a snack food which makes the most use of the ability of the oils and fat component to smoothly and easily melt in the mouth, which has light taste and texture and leaves a pleasing aftertaste in the mouth.

In addition, if the content of the oils and fats in the snack food is limited to a level of not more than 10%, as expressed in terms of the crude fat content, the resulting snack food has high quality and more specifically, it has a low oil and fat content and is favorable for the health-oriented people, in addition to the foregoing characteristic properties.

What is claimed is:

1. A method for preparing a snack food, comprising the subjecting dough for snack foods to a puffing treatment through hot-air drying, spraying or coating an adhesive liquid free of a flavoring material onto the puffed snack dough, adding a flavoring material to the dough, drying the resulting dough, and then incorporating, into the puffed snack dough, oils and fats having a saturated fatty acid content of not more than 40% of an unsaturated fatty acid content of not less than 50%, as an oil and fat component.

2. The method as set forth in claim 1 wherein the snack food comprises the oils and fats in an amount of not more than 10% by weight based on the total weight of the snack dough as expressed in terms of the amount of the crude oil.

3. The method as set forth in claim 2, wherein the snack food comprises the oils and fats in an amount of not more than 10% by weight based on the total weight of the snack dough as expressed in terms of the amount of the crude oil.

4. The method as set forth in claim 1, wherein the snack dough is pre-dried prior to the hot air-drying to control the moisture content of the dough to the range of from 4 to 10% by weight.

5. The method as set forth in claim 4, wherein the pre-drying step is carried out at a temperature ranging from 20 to 60° C. and a relative humidity ranging from 20 to 80% for a time of at least 10 hours.

6. The method as set forth in claim 1, wherein the hot air-drying step is carried out by the fluidized-bed method.

7. The method as set forth in claim 6, wherein the fluidized-bed method is carried out for 10 to 40 seconds using hot air having a temperature ranging from 200 to 300° C.

8. The method as set forth in claim 1, wherein the oil and fat component has a saturated fatty acid content of not more than 30% and an unsaturated fatty acid content of not less than 60%.

9. The method as set forth in claim 1, wherein the oil and fat component is olive oil.

10. The method as set forth in claim 1, which comprises pregelatinizing raw starch material and water through an extruder to prepare the dough.

11. The method as set forth in claim 10, wherein the extruder is a twin-extruder.

12. The method as set forth in claim 10, wherein the raw starch material is pregelatinized at a temperature of 100 to 180° C. for 5 to 40 seconds.

13. The method of claim 1, wherein the adhesive solution is a starch solution.

14. A method for preparing a snack food, comprising pre-drying dough for snack food to control the moisture content of the dough to the range of 4 to 10%, subjecting the resulting dough to a puffing treatment through hot-air drying, applying an adhesive liquid to the dough, further applying a flavoring material thereto, drying the resulting dough and then incorporating, into the puffed snack dough, oils and fats having a saturated fatty acid content of not more than 40% and an unsaturated fatty acid content of not less than 50%, as an oil and fat component to prepare the snack food containing the oils and fats in an amount of not more than 10% by weight based on the total weight of the snack dough as expressed in terms of the amount of the crude oil.

15. The method as set forth in claim 14, wherein the pre-drying step is carried out at a temperature ranging from 20 to 60° C. and a relative humidity ranging from 20 to 80% for a time of at least 10 hours.

16. The method as set forth in claim 14, wherein the hot air-drying step is carried out by the fluidized-bed method.

17. The method as set forth in claim 16, wherein the fluidized-bed method is carried out for 10 to 40 seconds using hot air having a temperature ranging from 200 to 300° C.

18. The method as set forth in claim 14, which comprises pregelatinizing raw starch material and water through an extruder to prepare the dough.

19. The method as set forth in claim 18, wherein the raw starch material is pregelatinized at a temperature of 100 to 180° C. for 5 to 40 seconds.

20. The method as set forth in claim 18, wherein the extruder is a twin-extruder.

21. The method of claim 14, wherein the adhesive solution is a starch solution.

22. A method for preparing a snack food, comprising the steps of subjecting dough for snack foods to a puffing treatment through hot-air drying, spraying or coating an adhesive liquid containing a flavoring material onto the puffed snack dough, drying the resulting dough, and then incorporating, into the puffed snack dough, oils and fats having a saturated fatty acid content of not more than 40% and an unsaturated fatty acid content of not less than 50%, as an oil and fat component.

23. The method of claim 22, wherein the adhesive solution is a starch solution.

* * * * *